US012639829B2

(12) United States Patent
Blaga et al.

(10) Patent No.: US 12,639,829 B2
(45) Date of Patent: May 26, 2026

(54) COMPUTER METHOD AND APPARATUS FOR TAGLESS TRACKING OF LIVESTOCK

(71) Applicant: The Main Branch, Inc., Woodinville, WA (US)

(72) Inventors: Octavian Alexandru Blaga, Chattanooga, TN (US); David Benjamin Scott, Woodinville, WA (US)

(73) Assignee: Synetic, Inc., Woodinville, WA (US)

( * ) Notice: Subject to any disclaimer, the term of this patent is extended or adjusted under 35 U.S.C. 154(b) by 239 days.

(21) Appl. No.: 18/537,899

(22) Filed: Dec. 13, 2023

(65) Prior Publication Data

US 2024/0202939 A1      Jun. 20, 2024

Related U.S. Application Data

(60) Provisional application No. 63/387,490, filed on Dec. 14, 2022, provisional application No. 63/387,488, (Continued)

(51) Int. Cl.
*G06T 7/246* (2017.01)
*A01K 11/00* (2006.01)
(Continued)

(52) U.S. Cl.
CPC ............ *G06T 7/246* (2017.01); *A01K 11/006* (2013.01); *A01K 29/005* (2013.01); *A61B 5/02416* (2013.01); *A61B 5/742* (2013.01); *G06T 5/70* (2024.01); *G06T 7/0012* (2013.01); *G06T 7/277* (2017.01); *G06T 7/73* (2017.01); *G06V 10/26* (2022.01); *G06V 10/30* (2022.01); *G06V 10/44* (2022.01); *G06V*

10/751 (2022.01); *G06V 10/764* (2022.01); *G06V 40/10* (2022.01); *A61B 2503/40* (2013.01); *G06T 2207/10016* (2013.01); (Continued)

(58) Field of Classification Search
CPC .... A01K 11/006; A01K 29/005; G06V 10/26; G06V 10/30; G06V 10/44; G06V 10/751; G06V 10/764; G06T 7/0012; G06T 7/73; G06T 7/246; G06T 7/277; G06T 2207/20221; G06T 2207/30004; G06T 2207/30232; A61B 5/02416; A61B 5/742; A61B 2503/40
See application file for complete search history.

(56) References Cited

U.S. PATENT DOCUMENTS

2019/0050926 A1*    2/2019  Cooper .................. H04W 4/021

FOREIGN PATENT DOCUMENTS

EP            4030395 A1 *  7/2022  ............. G06V 40/50

OTHER PUBLICATIONS

Cowton, et al. (Automated Individual Pig Localisation Tracking and Behaviour Metric Extraction Using Deep Learning). (Year: 2019).*
(Continued)

*Primary Examiner* — Daniel G Mariam
(74) *Attorney, Agent, or Firm* — PatentVest, Inc.; Matthew L. Bycer

(57) ABSTRACT

A computer method provides tagless tracking of livestock. Individual livestock are identified using biometric identification. Biometric identities are associated with digital identities. The method reconciles image analysis and tracking errors iteratively.

20 Claims, 6 Drawing Sheets

Related U.S. Application Data filed on Dec. 14, 2022, provisional application No. 63/387,491, filed on Dec. 14, 2022.

(51) Int. Cl.

| | |
|---|---|
| *A01K 29/00* | (2006.01) |
| *A61B 5/00* | (2006.01) |
| *A61B 5/024* | (2006.01) |
| *G06T 5/70* | (2024.01) |
| *G06T 7/00* | (2017.01) |
| *G06T 7/277* | (2017.01) |
| *G06T 7/73* | (2017.01) |
| *G06V 10/26* | (2022.01) |
| *G06V 10/30* | (2022.01) |
| *G06V 10/44* | (2022.01) |
| *G06V 10/75* | (2022.01) |
| *G06V 10/764* | (2022.01) |
| *G06V 40/10* | (2022.01) |

(52) U.S. Cl.
CPC ............... *G06T 2207/20221* (2013.01); *G06T 2207/30004* (2013.01); *G06T 2207/30232* (2013.01)

(56) References Cited

OTHER PUBLICATIONS

Ghoshal, et al. (A New approach for the eye detection of any living object with the help of Harris Corner Detector). (Year: 2012).*
Wee, et al. (Computer English Translation of Japanese Patent No. JP 2016-519941 A). (Year: 2016).*

* cited by examiner

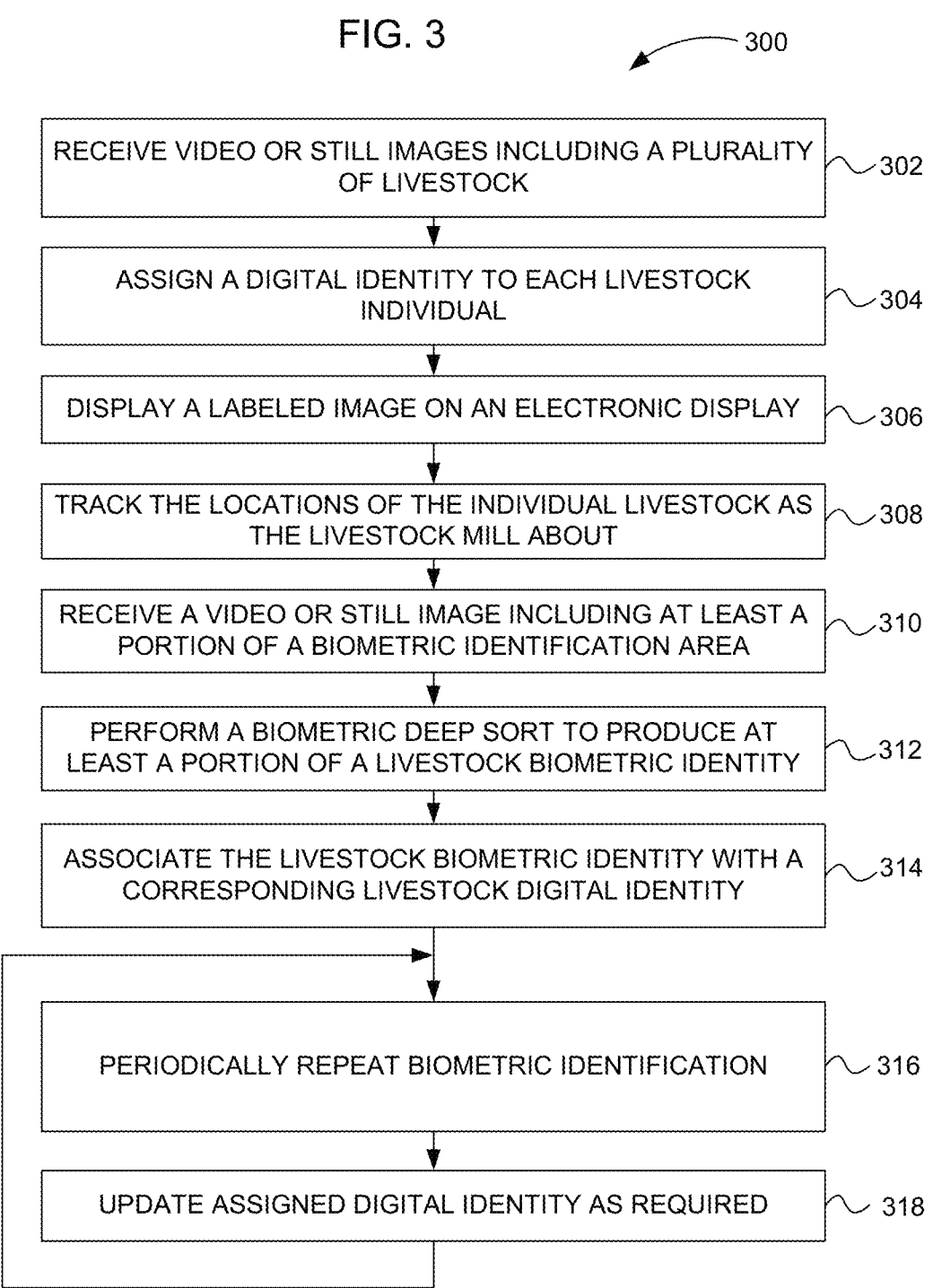

RECEIVE VIDEO OR STILL IMAGES INCLUDING A PLURALITY OF LIVESTOCK ~302

ASSIGN A DIGITAL IDENTITY TO EACH LIVESTOCK INDIVIDUAL ~304

DISPLAY A LABELED IMAGE ON AN ELECTRONIC DISPLAY ~306

TRACK THE LOCATIONS OF THE INDIVIDUAL LIVESTOCK AS THE LIVESTOCK MILL ABOUT ~308

RECEIVE A VIDEO OR STILL IMAGE INCLUDING AT LEAST A PORTION OF A BIOMETRIC IDENTIFICATION AREA ~310

PERFORM A BIOMETRIC DEEP SORT TO PRODUCE AT LEAST A PORTION OF A LIVESTOCK BIOMETRIC IDENTITY ~312

ASSOCIATE THE LIVESTOCK BIOMETRIC IDENTITY WITH A CORRESPONDING LIVESTOCK DIGITAL IDENTITY ~314

PERIODICALLY REPEAT BIOMETRIC IDENTIFICATION ~316

UPDATE ASSIGNED DIGITAL IDENTITY AS REQUIRED ~318

500

COMPUTER METHOD AND APPARATUS FOR TAGLESS TRACKING OF LIVESTOCK

CROSS REFERENCE TO RELATED APPLICATIONS

The present application claims benefit of U.S. Provisional Patent Application No. 63/387,490, entitled "COMPUTER METHOD AND APPARATUS FOR TAGLESS TRACK-ING OF LIVESTOCK", filed Dec. 14, 2022; U.S. Provisional Patent Application No. 63/387,491, entitled "METHOD AND SYSTEM FOR DETECTING LIVE-STOCK RESPIRATORY COMPROMISE", filed Dec. 14, 2022; and U.S. Provisional Patent Application No. 63/387,488, entitled "LIVESTOCK HEART RATE MONITOR-ING", filed Dec. 14, 2022 herewith.

The foregoing applications, to the extent not inconsistent with the disclosure herein, are incorporated by reference.

SUMMARY

According to an embodiment, a computer method for tagless tracking of livestock and biometric identification includes receiving, into a computer a first digital video or sequence of digital photographic frames from one or more digital image capture devices. The first digital video or sequence of digital photographic frames includes a plurality of livestock locations in a pen. A digital identity is assigned to each livestock individual in the pen. Locations of the livestock individuals are tracked as the livestock mill about. The computer method further includes receiving a second digital video or digital photographic frame including at least a portion of a biometric identification area of an individual livestock body. A biometric deep sort is performed to produce at least a portion of an individual livestock biometric identity. The individual livestock biometric identity is associated with the corresponding livestock digital identity.

BRIEF DESCRIPTION OF THE DRAWINGS

FIG. 3 is a flowchart showing a computer method for livestock biometric identification and tracking, according to an embodiment.

DETAILED DESCRIPTION

Figure 1:
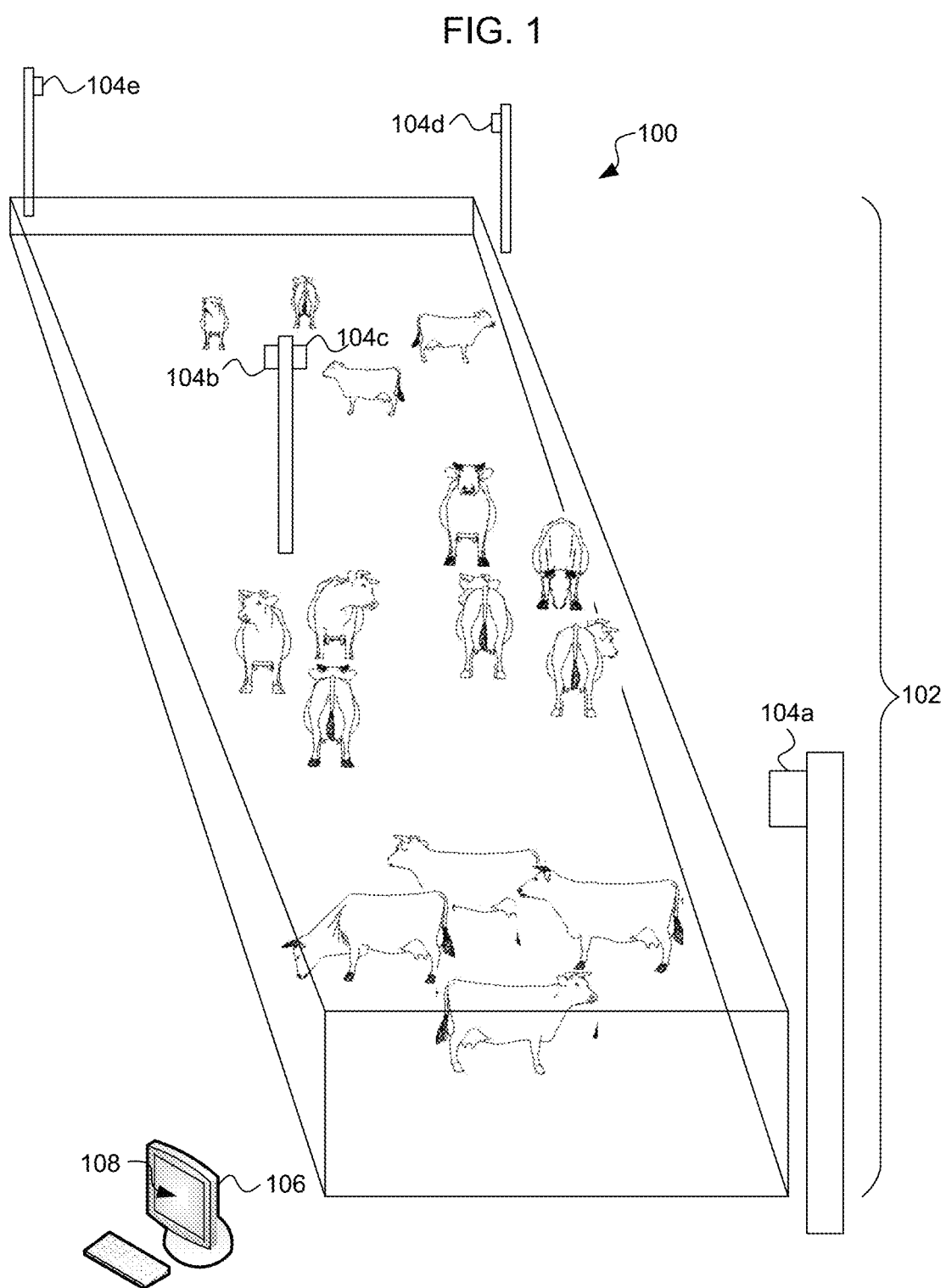
FIG. 1 is a diagram of livestock in a pen, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 is a diagram of a system 100 for monitoring livestock health, according to an embodiment. A plurality of livestock 102 may be constrained by a peripheral fence, for example in a feedlot. The computer methods described herein may be performed on such a peripherally constrained plurality of livestock, or may be performed on livestock with no nearby constraint.

A plurality of sensors 104, here shown as cameras 104a, 104b, 104c, 104d, 104e, are disposed to obtain digital video or sequences of still frames including the livestock 102. The digital video or sequences of still frames are transmitted to a computer 106. The computer 106 may process the digital video or sequences of still frames as described below. The computer 106 may display the videos or sequences of still frames on an electronic display 108 for viewing by a user. Additionally or alternatively the computer 106 may display other indicia, optionally overlaying the fields of view, derived from processing described below.

Figure 2:
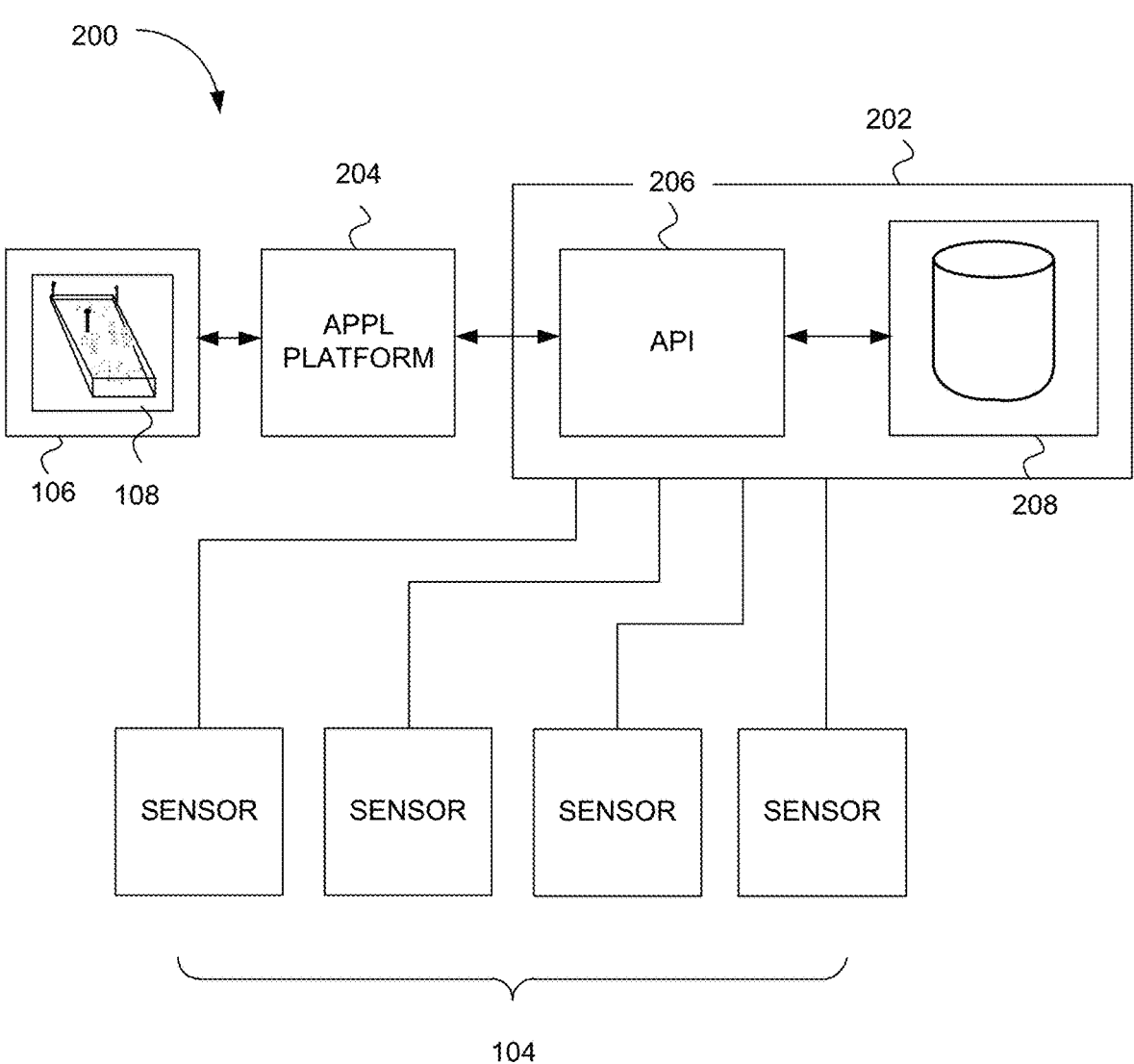
FIG. 2 is a block diagram of a computer system for tagless tracking and biometric identification of livestock in a pen, according to an embodiment.

FIG. 2 is a block diagram of a computer system for tagless tracking and biometric identification of livestock, according to an embodiment. The cameras 104a, 104b, 104c, 104d, 104e are indicated as sensors 104. The sensors 104 may optionally include other sensing modalities in addition to focal plane imaging. Optionally, the sensors 104 are configured to provide hyper-spectral imaging. The sensors are operatively coupled to a computer 202. As shown in FIG. 2, the computer 106 shown in FIG. 1 may be configured as a client or peer device. Optionally all processing described herein may be performed in a single computer 106. The computer 106 may include a thin client, a portable or non-portable computer, a personal electronic device such as a smart phone, or other platform capable of receiving data and driving an electronic display 108.

The computer 202 may be a server computer, and/or may include a server farm, a set of pipelined servers, relay servers, etc. as is known in the art of computer networking. The server 202 may receive data from the sensors 104 and process the data as describe herein. The server may include an application program interface (API) portion 206 operatively coupled to an application platform 204. The application platform 204 may be included in the server 202, may be included in the local computer 106, or may be otherwise operatively coupled therebetween. The server 202 (and/or computer 106) include a non-transitory computer readable memory 208 such as a rotating disk or solid state memory. The non-transitory computer readable memory may support a database, look-up table, or other software structure to enable storage and retrieval of information described below. Typically, the computer 202 includes a microprocessor, memory, and other components appropriate for performing image processing on the data received from the sensors 104.

Figure 5:
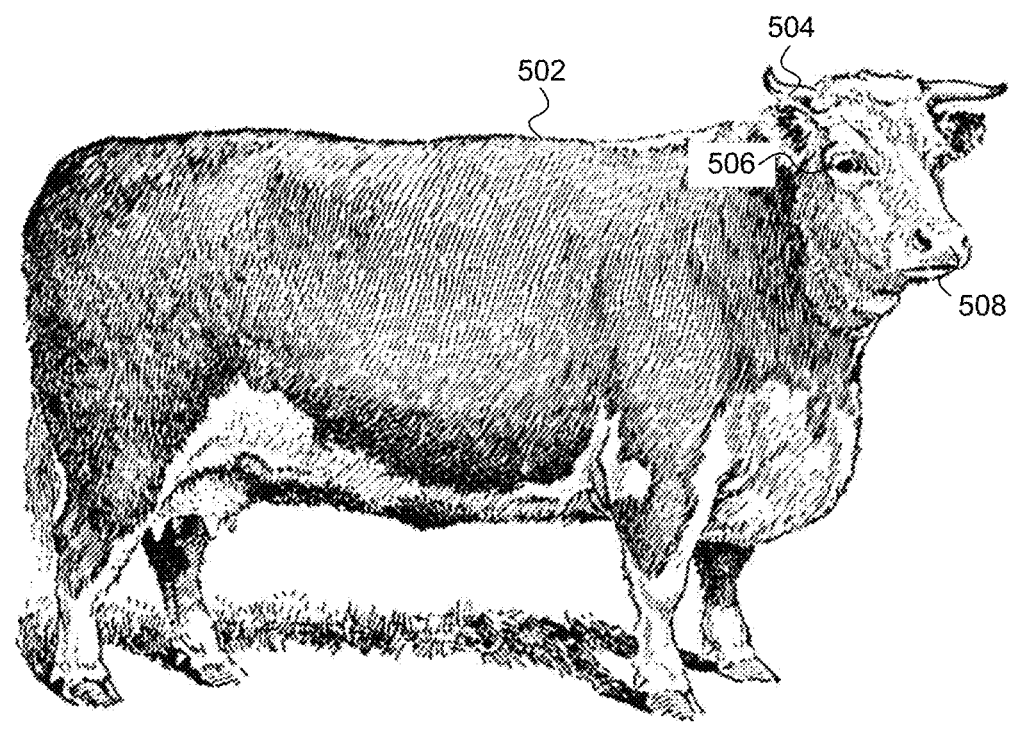
FIG. 5 is a diagram of an individual livestock with biometric markers for determining a biometric identity, according to an embodiment.

FIG. 3 is a flow chart showing a computer method 300 for livestock tracking and biometric identification, according to an embodiment which includes, at step 302, receiving, into a computer 106, 202, a first digital video or sequence of digital photographic frames from one or more digital image capture devices 104a, 104b, 104c, 104d, 104e. The digital image capture devices 104a, 104b, 104c, 104d, 104e may be referred to, collectively or individually, as 104 herein. The first digital video or sequence of digital photographic frames may include a plurality of livestock locations in a pen 102. Proceeding to step 304, a digital identity is assigned to each livestock individual in the pen. In step 308, locations of the livestock individuals are tracked as the livestock mill about. Referring to FIGS. 3 and 5, the method 300 may further include, at step 310, receiving a second digital video or digital photographic frame 500 including at least a portion of a biometric identification area 504, 506, 508 of an individual livestock body 502. A biometric deep sort is performed in step 312 to produce at least a portion of an individual livestock biometric identity. Proceeding to step 314, the individual livestock biometric identity is associated with a corresponding livestock digital identity. Step 314 may, for example, include associating the biometric and digital identities in a look up table, database, or other logical construct stored on a non-transitory computer readable medium.

Figure 4:
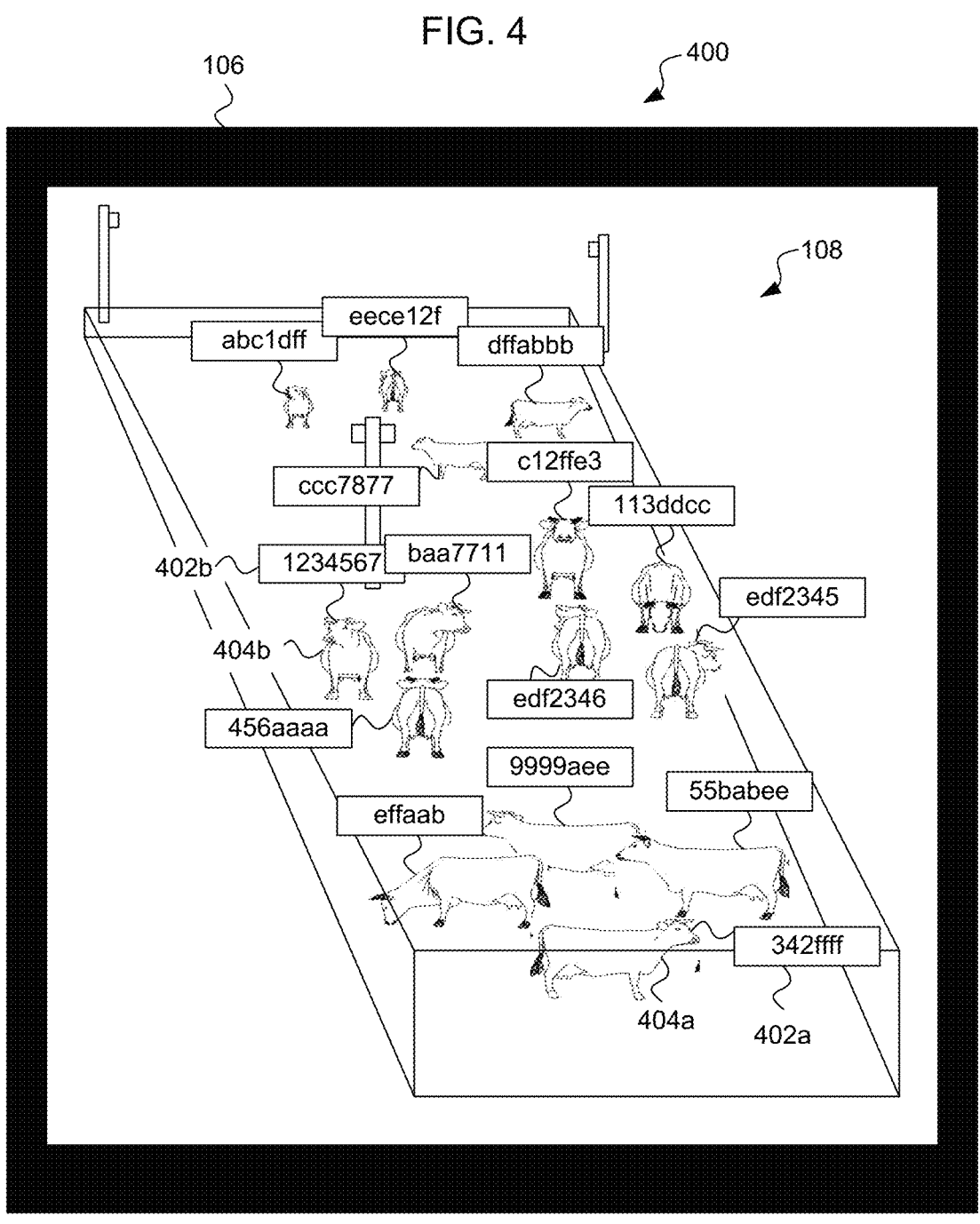
FIG. 4 is a diagram of information including livestock milling about with respective electronic identities output to an electronic display, according to an embodiment.

Referring to FIGS. 3 and 4, the method 300 may further include, in step 306, displaying a labeled image 400 on an electronic display 108, the labeled image including the current digital identities 402 corresponding each livestock individual.

According to an embodiment, tracking locations of the livestock individuals as the livestock mill about, in step 308, is performed using a Kalman filter. According to embodiments, tracking the locations of the livestock individuals may employ at least some parts of simultaneous localization and mapping (SLAM) which uses the Kalman filter. SLAM is usually used in robotics so the robot knows where in the environment it is located based on a few measurements.

In standard SLAM, the robot sends some lasers or pings in the environment to figure out where it is, based on a few reference points. In the present embodiment, if one uses multiple poles, each supporting a digital camera or video device, the pole locations serve as reference points from which the computer method, and specifically step 308, obtains measurements of the location and velocity of each detected class. In this case, the detected class is "livestock". With measurements from one or many poles, step 308 includes calculating a probability that a particular detected livestock individual is the same detected livestock individual from a previous few frames. The more poles there are, the more accurate the measurements will be for both tracking and identification.

Referring to FIG. 5, receiving, in step 310, the second digital video or digital photographic frame including at least a portion of a biometric identification area of an individual livestock body may include receiving a plurality of frames. According to an embodiment, performing the biometric deep sort further includes operating a Harris filter to locate livestock biometric markers. The Harris filter identifies corners in the frame, the corners being associated with the biometric markers. Performing the biometric deep sort in step 312 may include identifying, on a grid, relative locations of individual livestock biometric markers and storing the grid locations in an individual livestock biometric identity record in a livestock population model.

The individual livestock biometric markers may include at least two of a corner of an eye, a corner formed by a horn, a corner formed by an ear, a snout corner, a hide color corner, a hoof corner, and/or a tail corner. Identifying individual biometric markers may include assigning classes of livestock body surface features and performing a semantic segmentation to classify each pixel as belonging to a livestock body surface feature. Assigning classes of livestock body surface features may include assigning livestock eye, livestock horn, livestock ear, livestock snout, livestock hide color patterns, livestock hoof, and/or livestock ear classes. Assigning classes of livestock body surface features may include assigning livestock eye corners and assigning livestock snout corners. Assigning classes of livestock body surface features may include assigning contrasting locations of skin and/or fur coloration. To perform identification, the computer method includes receiving a high resolution snapshot at a given time at which all heads, eyes, and snouts, are detected. Step 312 may include computing all face geometries. In step 314, the computer method 300 may include performing a probability computation against the database to get the most likely candidate electronic IDs corresponding to the biometric IDs. If a good candidate is obtained, the ID of that candidate may be assigned to the data recorded for the aforementioned detection. If multiple candidates are obtained, the multiple candidates, as well as secondary candidates, may be set to be reviewed during subsequent algorithm improvement iterations.

The first digital video or sequence of digital photographic frames received in step 302 may include a wider angle view including a plurality of livestock in the frame, compared to the second digital video or sequence of digital photographic frames includes a narrower angle view that includes less than all of the plurality of livestock in the frame. The narrower angle view may primarily include at least a portion of an individual livestock. In an embodiment, the narrower angle view consists essentially of the biometric identification area (e.g., see FIG. 5, 504, 506, 508) of the individual livestock's body 502.

The method 300 may further include receiving a third digital video or sequence of digital photographic frames including plurality of livestock locations in the pen as the livestock mill about, the plurality of livestock having corresponding digital identities and at least a portion of the plurality of livestock having been assigned a biometric identity. The individual livestock may be tracked (see step 308) as the livestock mill about, the individual livestock nominally being assigned livestock digital identities. The method 300 may further include receiving the second digital video or digital photographic frame corresponding to one of the individual livestock and including at least a portion of the biometric identification area of the individual livestock body, performing, in step 316, a second biometric identification of the individual livestock; and, in step 318, verifying that the tracked individual livestock is the individual livestock associated with the current livestock digital identity.

According to an embodiment, the method 300 may include tracking the individual livestock as the livestock mill about in step 308, the individual livestock nominally being assigned livestock digital identities, receiving the second digital video or digital photographic frame corresponding to one of the individual livestock and including at least a portion of the biometric identification area of the individual livestock body (see step 310), and performing biometric identification of the individual livestock.

The method 300 may include determining the individual livestock does not match a biometric identity of a known individual livestock. If an individual livestock has not been biometrically identified, the method 300 may include performing the biometric deep sort (see step 312) to produce at least a portion of an individual livestock biometric identity, and (referring to step 314), associating the individual livestock biometric identity with the corresponding livestock digital identity. This may be used to gradually match individual livestock digital identities to individual livestock biometric identities after beginning tracking the livestock as the livestock mill about.

Improvement of the biometric identity may be obtained by determining that the biometric identity includes biometric markers not previously included in the biometric identity of the individual livestock (not shown) and augmenting the biometric identity with the additional biometric markers.

Figure 6:
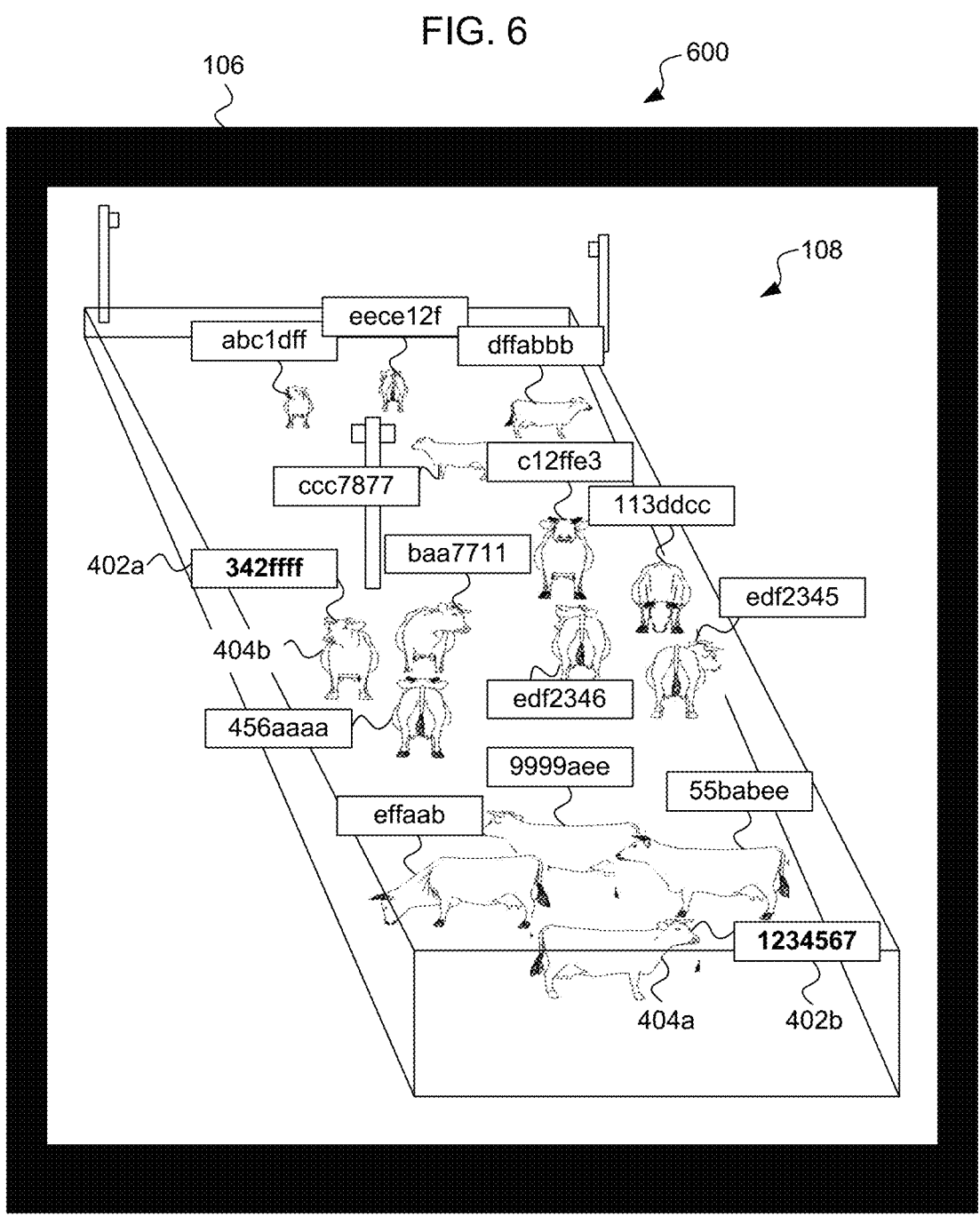
FIG. 6 is a diagram showing an electronic display where an electronic identity is adjusted to correspond to a biometric identity, according to an embodiment.

Referring to FIG. 6, the individual livestock may be partially or completely obscured as the livestock mill about. The method 300 may include determining that the tracked individual livestock 404*a* is an individual livestock associated with a different individual livestock digital identity 402*b* than an incorrect livestock digital identity 402*a* currently assigned to the first individual livestock 404*a*. The method 300 may then include, in step 318, assigning the correct individual livestock digital identity to the individual livestock. For example, comparing FIG. 4 to FIG. 6, see that individual livestock 404*a*, was incorrectly associated with digital identity 402*a* "342ffff". Upon the biometric deep sort, the individual livestock 404*a*, was found to have been assigned the digital identity associated with a different livestock 404*b*. Step 318 may include assigning the correct livestock digital identity 402*b* "1234567" previously associated with a different individual livestock 404*b* than the individual livestock 404*a*. Step 318 may include assigning the incorrect livestock digital identity 402*a* "342ffff" previously associated with the first individual livestock 404*a* to a second individual livestock 404*b*.

The livestock may be cows and/or steers, for example.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A computer method for livestock tracking and biometric identification, comprising:

receiving, into a computer, a first digital video or sequence of digital photographic frames from one or more digital image capture devices, the first digital video or sequence of digital photographic frames including a plurality of livestock locations;

assigning a digital identity to each livestock individual;

tracking locations of the livestock individuals as the livestock mill about;

receiving a second digital video or digital photographic frame including at least a portion of a biometric identification area of an individual livestock body;

performing a biometric deep sort to produce at least a portion of an individual livestock biometric identity, whereby said step of performing comprises identifying, on a grid, relative locations of individual livestock biometric markers, and storing the grid locations in an individual livestock biometric identity record in a livestock population model; and associating the individual livestock biometric identity with the corresponding livestock digital identity.

2. The computer method of claim 1, further comprising:

displaying a labeled image on an electronic display, the labeled image including the current digital identities corresponding each livestock individual.

3. The computer method of claim 1, wherein tracking locations of the livestock individuals as the livestock mill about is performed using a Kalman filter.

4. The computer method of claim 1, wherein performing the biometric deep sort further comprises operating a Harris feature to locate livestock biometric markers.

5. The computer method of claim 1, wherein the individual livestock biometric markers include at least two selected from the group consisting of a corner of an eye, a corner formed by a horn, a corner formed by an ear, a snout corner, a hide color corner, a hoof corner, and a tail corner.

6. The computer method of claim 1, wherein identifying individual biometric markers includes:

assigning classes of livestock body surface features; and performing a semantic segmentation to classify each pixel as belonging to a livestock body surface feature.

7. The computer method of claim 6, wherein assigning classes of livestock body surface features includes assigning livestock eye and livestock snout classes.

8. The computer method of claim 6, wherein assigning classes of livestock body surface features includes assigning livestock eye corners and assigning livestock snout corners.

9. The computer method of claim 1, wherein the first digital video or sequence of digital photographic frames includes a wider angle view including a plurality of livestock in the frame; and wherein the second digital video or sequence of digital photographic frames includes a narrower angle view that includes less than all of the plurality of livestock in the frame.

10. The computer method of claim 9, wherein the narrower angle view primarily includes at least a portion of an individual livestock.

11. The computer method of claim 9, wherein the narrower angle view consists essentially of the biometric identification area of the individual livestock's body.

12. The computer method of claim 1, further comprising:

tracking an individual livestock as the livestock mill about, the individual livestock nominally being assigned a livestock digital identity;

performing a second biometric identification of the individual livestock; and verifying that the tracked individual livestock is the individual livestock associated with the livestock digital identity.

13. The computer method of claim 1, further comprising:

tracking individual livestock as the livestock mill about, the individual livestock nominally being assigned livestock digital identities;

receiving the second digital video or digital photographic frame corresponding to one of the individual livestock and including at least a portion of the biometric identification area of the individual livestock body;

performing biometric identification of the individual livestock;

determining the individual livestock does not match a biometric identity of an individual livestock and associating the individual livestock biometric identity with the corresponding livestock digital identity.

14. The computer method of claim 1, further comprising:

tracking a first individual livestock as the livestock mill about, the first individual livestock nominally being assigned a livestock digital identity;

performing biometric identification of the first individual livestock;

determining that the tracked first individual livestock is an individual livestock associated with a different livestock digital identity than an incorrect livestock digital identity currently assigned to the first individual livestock; and assigning the correct livestock digital identity to the first individual livestock.

15. The computer method of claim 14, further comprising:

assigning the incorrect livestock digital identity previously associated with the first individual livestock to a second individual livestock.

16. The computer method of claim 1, wherein the livestock are cows and/or steers.

17. A computer method for livestock tracking and biometric identification, comprising:

receiving, into a computer, a first digital video or sequence of digital photographic frames from one or more digital image capture devices, the first digital video or sequence of digital photographic frames including a plurality of livestock locations;

assigning a digital identity to each livestock individual;

tracking locations of the livestock individuals as the livestock mill about;

receiving a second digital video or digital photographic frame including at least a portion of a biometric identification area of an individual livestock body;

performing a biometric deep sort to produce at least a portion of an individual livestock biometric identity;

associating the individual livestock biometric identity with the corresponding livestock digital identity:

tracking an individual livestock as the livestock mill about, the individual livestock nominally being assigned a livestock digital identity;

performing biometric identification of the individual livestock;

determining that the biometric identity includes biometric markers not previously included in the biometric identity of the individual livestock; and augmenting the biometric identity with the additional biometric markers.

18. The computer method of claim 17, wherein the first digital video or sequence of digital photographic frames includes a wider angle view including a plurality of livestock in the frame; and wherein the second digital video or sequence of digital photographic frames includes a narrower angle view that includes less than all of the plurality of livestock in the frame.

19. The computer method of claim 18, wherein the narrower angle view primarily includes at least a portion of an individual livestock.

20. The computer method of claim 18, wherein the narrower angle view consists essentially of the biometric identification area of the individual livestock's body.

* * * * *